(12) United States Patent
Lindner

(10) Patent No.: US 9,872,490 B2
(45) Date of Patent: Jan. 23, 2018

(54) AGROCHEMICAL COMPOSITIONS

(75) Inventor: Gregory J. Lindner, Wilmington, DE (US)

(73) Assignee: Croda Americas LLC, Wilmington, DE (US)

( * ) Notice: Subject to any disclaimer, the term of this patent is extended or adjusted under 35 U.S.C. 154(b) by 407 days.

(21) Appl. No.: 12/450,777

(22) PCT Filed: Apr. 11, 2008

(86) PCT No.: PCT/US2008/004721
§ 371 (c)(1),
(2), (4) Date: Mar. 1, 2010

(87) PCT Pub. No.: WO2008/127661
PCT Pub. Date: Oct. 23, 2008

(65) Prior Publication Data
US 2010/0160168 A1    Jun. 24, 2010

Related U.S. Application Data

(60) Provisional application No. 60/907,648, filed on Apr. 12, 2007.

(51) Int. Cl.
*A01N 25/02*   (2006.01)

(52) U.S. Cl.
CPC .................... *A01N 25/02* (2013.01)

(58) Field of Classification Search
CPC ...................................... A01N 25/02
USPC ....................................... 504/362
See application file for complete search history.

(56) References Cited

U.S. PATENT DOCUMENTS

| | | | | |
|---|---|---|---|---|
| 5,078,782 A | * | 1/1992 | Nielsen et al. | 504/135 |
| 5,360,783 A | * | 11/1994 | Itoh et al. | 504/305 |
| 6,165,939 A | * | 12/2000 | Agbaje | A01N 25/04 504/105 |
| 6,586,366 B1 | | 7/2003 | Auda et al. | |
| 6,667,276 B1 | | 12/2003 | Maier et al. | |
| 2005/0164887 A1 | | 7/2005 | Killick et al. | |
| 2006/0063676 A1 | | 3/2006 | Brigance et al. | |

FOREIGN PATENT DOCUMENTS

| | | |
|---|---|---|
| EP | 0388239 | 9/1990 |
| WO | WO 2004/080177 | 9/2004 |

OTHER PUBLICATIONS

International Search Report dated Jul. 14, 2008 for PCT/US2008/004721.
European Search Report dated Dec. 3, 2012 for corresponding EP 08742793.6.

* cited by examiner

*Primary Examiner* — Sreenivasan Padmanabhan
(74) *Attorney, Agent, or Firm* — RatnerPrestia

(57) ABSTRACT

Homogeneous stable liquid agrochemical concentrate formulations which form stable dilutions with water comprises biologically efficacious oil, water, agrochemical dissolved in the water to form concentrated aqueous electrolyte, a stabilizing surfactant, based on non-ionic or non-ionic and anionic or amphoteric surfactant, comprising oil compatible, electrolyte tolerant surfactant and water soluble, electrolyte tolerant surfactant and optionally a polyol component, are useful as tank mix adjuvants. The formulations combine biologically efficacious oil, e.g. crop oil, with an electrolyte agrochemical, particularly water soluble non-selective herbicide such as glyphosate, or electrolyte nutrients particularly water soluble inorganic fertilizers providing nutrients such as nitrogen, phosphorus, potassium or sulphur.

8 Claims, No Drawings

AGROCHEMICAL COMPOSITIONS

CROSS REFERENCE TO RELATED APPLICATIONS

This application is the National Phase application of International Application No. PCT/US2008/004721, filed Apr. 11, 2008, which designates the United States and was published in English, which further claims the benefit of priority from U.S. Provisional Application No. 60/907,648, filed Apr. 12, 2007. The foregoing related applications, in their entirety, are incorporated into the present application by reference.

This invention relates to agrochemical compositions and particularly to homogeneous concentrates which form stable dilutions with water, and which include oils and electrolyte agrochemicals such as fertilizer electrolytes or electrolyte pesticides.

Agrochemical compositions can provide nutrients, growth regulators and/or pesticides, e.g. herbicides, insecticides, fungicides or acaricides. To reduce their overall cost in use spray adjuvants are added to water based agrochemical spray mixtures. Various spray adjuvants are in commercial use to provide effects including foam control, increased agrochemical effectiveness, and/or spray mixture modification. Many spray adjuvants, particularly in the United States, are supplied as, especially concentrated, liquids, for example self-emulsifying oil/surfactant compositions—so-called crop oil concentrates (COCs), or readily water soluble or dispersible surfactant formulations—known as concentrated liquid non-ionic surfactants (NIS).

Spray components may include electrolytes e.g. plant nutrients (fertilizers), electrolyte agrochemical actives and other inorganic spray mixture additives. Plant nutrients are typically supplied as bulk solids or concentrated dense aqueous solutions usually at or near saturation, commonly called Liquid Fertilizers (LF). Their high concentration of dissolved electrolyte makes combining LFs with other adjuvant components in high concentration spray solutions challenging because including LFs can result in physical instability or incompatibility of the resulting mixture of pesticide alone or in combination with COC, NIS, and LF products. There are many complex processes producing such incompatibility including coalescence, creaming, sedimentation, flocculation, and heteroflocculation.

COCs typically contain from 60 to 90% (by volume) of agricultural oil or crop oil, and usually include oil soluble emulsifier, typically a blend of anionic and/or nonionic surfactants, that enables self-emulsification of the oil on dilution in water based spray mixtures, typically, at a total surfactant concentration of 1 to 40%, more usually 10 to 17% of the COC. COCs are a cost effective way of including such oils in water based e.g. emulsion, formulations because they are highly concentrated, reducing transport costs, and the disadvantages of water based, particularly emulsion, concentrate formulations, particularly complex development and manufacture, the need to include thickeners, preservatives, and anti-freeze additives (such emulsions may support microbial growth, cream, settle or sediment, and deteriorate over time particularly following freezing and thawing).

Recent improvements in COC cost-effectiveness include increasing the total concentration of oil compatible surfactant emulsifier, from 12-17% about ten years ago to currently about 40%, reducing the area application rate; and/or the selection of specific surfactant types, to give improved performance of the COCs with specific pesticide products.

PCT Published application WO 95/03881 A describes a stable homogeneous COC containing oil, hydrocarbyl saccharide surfactant, and additional non-ionic surfactant that emulsifies readily on dilution in water e.g. in tank mixes giving better weed control with glyphosate salts.

U.S. Pat. No. 5,945,377 describes aqueous spray postemergence herbicide compositions including monosaccharide, particularly fructose, to potentiate herbicidal activity without reducing tolerance of a crop plant to the herbicide.

U.S. Pat. No. 6,589,913 describes glyphosate formulations including lipophilic solvent, lipophobic plant nutrient and oil soluble base which forms a lipophilic solvent soluble complex with glyphosate assisting coupling of the lipophobic plant nutrient and lipophilic solvent. Relatively low concentrations of aqueous electrolyte are described and oil soluble amine salts i.e. cationic surfactants are the only surfactants described as effecting formulation of such compositions.

U.S. Pat. No. 5,356,861 (also U.S. Re-issue 36149) relates to homogeneous aqueous blends of ammonium sulfate and alkyl polysaccharide as the sole surfactant in tank mix adjuvants with glyphosate as herbicide particularly against broadleaf weeds, but does not contemplate including oils in the spray mixture.

U.S. Pat. No. 6,117,820 is directed to aqueous agrochemical concentrates comprising agrochemical electrolyte e.g. salts of glyphosate, fomesafen, glufosinate, paraquat or bentazone; alkoxylated adjuvant; alkylglycoside and co-surfactant, which forms a structured aqueous system with the alkylglycoside. Again this document does not contemplate including oils in the spray mix.

U.S. Pat. No. 6,255,253 describes agrochemical microemulsions with 80% having a droplet size from 10 to 100 nm, containing: alkyl(oligo)glycoside; and oil phase containing: organic water insoluble solvent; and water insoluble agrochemical.

WO 04/100661 A describes COCs including crop oil, saccharide adjuvant, and surfactant combined with water giving a robust, single phase composition allowing delivery of highly concentrated liquid agricultural adjuvant product with a total surfactant concentration similar to those in use today (ca. 10-40% w/w). The saccharide inclusion improves adjuvant formulation cost-effectiveness and enables provision of one very broadly effective adjuvant combining preferred characteristics of the COC, NIS, and newer saccharide adjuvant types.

As indicated by the above prior art, many improved COCs though themselves stable have tended not to be stable when combined directly with highly concentrated electrolyte, and such combined concentrate formulations are nowhere described or hinted at in any of the prior art listed above. This has generally led to separate additions of COCs and electrolyte components to aqueous spray formulations in so-called tank mixes e.g. as described in WO 04/100661 A. Desirable electrolytes include inorganic fertilizers and electrolyte actives particularly pesticides. Using COCs as tank mix additives provides desired adjuvant activity in the spray, but involves adding at least two separate tank mix components. It is recognised that a single concentrate would give significant user advantages, especially simplifying spray mix make up and minimizing product incompatibility.

The present invention is based on a development of COC type concentrates which can stably include substantial electrolyte concentrations, are amenable to bulk handling, and yet readily disperse to form emulsions on dilution with water and/or additional electrolyte solution in a spray mix. Particularly desirable properties sought in these concentrates include stability under cold (0° C.), ambient (typically about 20 to 25° C.), and high temperature (e.g. about 50° C.) conditions, low fluid viscosity, and ready emulsification on dilution into water. Further desirable attributes include rapid dispersion upon dilution in both colder waters (at or near 4° C.) and predissolved electrolyte, low spray mix surface tension, rapid wetting of agricultural substrates and foam control both in the concentrate and on dilution to a spray mix.

Accordingly, the present invention provides an agrochemical concentrate formulation which is a homogeneous stable liquid which is capable of forming a stable dilution with water and which comprises:
a) at least one biologically efficacious oil;
b) water;
c) at least one agrochemical which is dissolved in the water to form a concentrated aqueous electrolyte;
d) a stabilizing surfactant composition, based on non-ionic or non-ionic and anionic or amphoteric surfactant(s), comprising at least one oil compatible, electrolyte tolerant surfactant and at least one water soluble, electrolyte tolerant surfactant; and
e) optionally at least one polyol component.

The invention particularly addresses the provision of concentrates including plant nutrient (fertilizer) and/or pesticide or, and particularly, herbicide materials. Accordingly the invention includes:
i) an agrochemical concentrate formulation which is a homogeneous stable liquid which is capable of forming a stable dilution with water and which comprises:
  a) at least one biologically efficacious oil,
  b) water,
  c) at least one plant nutrient material which is dissolved in the water to form a concentrated aqueous electrolyte,
  d) a stabilizing surfactant composition, based on non-ionic or non-ionic and anionic or amphoteric surfactant(s), comprising at least one oil compatible, electrolyte tolerant surfactant and at least one water soluble, electrolyte tolerant surfactant, and
  e) optionally at least one polyol component;
and
ii) an agrochemical concentrate formulation homogeneous stable liquid which is capable of forming a stable dilution with water and which comprises:
  a) at least one biologically efficacious oil,
  b) water,
  c) at least one pesticide or herbicide which is a dissolved in the water to form concentrated aqueous electrolyte,
  d) a stabilizing surfactant composition, based on non-ionic or non-ionic and anionic or amphoteric surfactant(s), comprising at least one oil compatible, electrolyte tolerant surfactant and at least one water soluble, electrolyte tolerant surfactant, and
  e) optionally at least one polyol component.

It is particularly desirable to use proportions of the components of the formulation within specific ranges and the present invention therefore includes an agrochemical concentrate formulation which is a homogeneous stable liquid which is capable of forming a stable dilution with water and which comprises:
a) from 1 to 50% by weight of at least one biologically efficacious oil;
b) from 20 to 60% by weight of water.
c) from 5 to 50% by weight of at least one agrochemical which is a dissolved in the water to form concentrated aqueous electrolyte;
d) from 1 to 25% by weight of a stabilizing surfactant composition, based on non-ionic or non-ionic and anionic or amphoteric surfactant(s), comprising at least one oil compatible, electrolyte tolerant surfactant and at least one water soluble, electrolyte tolerant surfactant; and
e) optionally from 1 to 40% by weight of at least one polyol component.

Generally concentrates of the invention will be diluted with water to produce agrochemical containing spray mixes. Such spray mixes will contain one or more pesticidally active ingredients and/or herbicidally active ingredients and/or nutrients. The invention accordingly includes a concentrate of the invention which has been diluted with water, particularly from 10 to 10000, especially from 10 to 1000, parts water per part concentrate. The invention also includes a method of making an agrochemical spray formulation which comprises diluting a concentrate of the invention with water, particularly from 10 to 10000, especially from 10 to 1000 parts water per part concentrate. If desired, further electrolyte solution e.g. as concentrated electrolyte solution, particularly from 1 to 1000 parts electrolyte solution per part concentrate, may be added to the concentrate before dilution with water. The final overall rate of dilution is typically from 10 to 10000 parts water and further electrolyte solution per part concentrate.

The (diluted) formulations will generally be used to treat crops (or land where crops are to be grown) including to fertilize crops and to kill weeds in or pests on crops.

The invention accordingly includes the use of such (diluted) formulations to treat crops including to fertilize crops and to kill weeds in crops or pests on crops and further provides a method of treating crops or soil adjacent to crop plants or soil in which crops are to be grown with a spray formulation which is or includes a diluted agrochemical concentrate formulation which is a homogeneous stable liquid which is capable of forming a stable dilution with water and which comprises:
a) at least one biologically efficacious oil;
b) water;
c) at least one agrochemical which is dissolved in the water to form a concentrated aqueous electrolyte;
d) a stabilizing surfactant composition, based on non-ionic or non-ionic and anionic or amphoteric surfactant(s), comprising at least one oil compatible, electrolyte tolerant surfactant and at least one water soluble, electrolyte tolerant surfactant; and
e) optionally at least one polyol component.

The invention is particularly directed to concentrate compositions that are homogeneous and form stable dilutions with water. By homogeneous we mean that the concentrate remains visibly homogeneous (optically clear) and stable for at least 24 hours, desirably for considerably longer e.g. up to 3 months, and sometimes longer. In this context, the concentrate is being considered free from deliberately added disperse phase components such as particulate solids or silicones e.g. present as antifoams (which may undergo dilution induced phase instability), as such deliberately included disperse phase components would be likely to make the concentrate hazy, milky or opaque.

In describing the concentrate as forming a stable dilution with water we mean that the concentrate forms a solution, microemulsion, or emulsion on simple mixing with the dilution water. When the product on dilution is an emulsion (or microemulsion) such compositions may be described as self emulsifying.

The term "biologically efficacious oil" means that the oil either itself has desired biological effects or that the oil is a carrier or solvent for a material with desired biological effects.

The term "stabilising surfactant" refers to a combination of at least one oil compatible electrolyte tolerant surfactant and at least one water soluble, electrolyte tolerant surfactant, which in combination stabilise the combination of the oil and the electrolyte solution to give a fluid homogeneous concentrate.

The oil component typically has a boiling point of over about 200° C. at atmospheric pressure and a melting point typically not higher than about 60° C. It may be or include mineral oil e.g. petroleum oil; silicone oil; optionally hydrogenated vegetable oil, such as optionally hydrogenated coconut, corn, cotton seed, linseed, mustard, neem, niger seed, oiticica, olive, palm, palm kernel, peanut, perilla, poppy seed, rape, particularly canola, seed, safflower, sesame, soybean or sunflower oil; or ester oil. Suitable ester oils include methylated or ethylated seed oils; esters of $C_1$ to $C_8$ alcohols with $C_8$ to $C_{22}$, particularly $C_{12}$ to $C_{18}$, fatty acids e.g. methyl, ethyl propyl and/or 2-ethylhexyl esters of caprylic, capric, lauric, myristic, palmitic, palmitoleic, stearic, iso-stearic, oleic, linoleic and/or linolenic acid(s), especially where such esters have a total of not more than 20 carbon atoms, and are preferably esters of $C_{12}$ to $C_{15}$ fatty acid, e.g. methyl, ethyl and/or propyl esters of lauric acid; and esters of $C_1$ to $C_8$ aliphatic or aromatic acids with $C_1$ to $C_{22}$ linear or branched alcohols e.g. isodecyl or isotridecyl acetate and/or isopropyl or 2ethylhexyl benzoate.

Typically the oil will form 0.5 to 50, more usually 5 to 40, particularly 10 to 35, % by weight of the total concentrate composition.

The stabilising surfactant is a combination of an oil compatible, electrolyte tolerant surfactant component and a water soluble, electrolyte tolerant surfactant component which stabilises the combination of the oil and the electrolyte solution to give a homogeneous concentrate. Desirably the stabilising surfactant combination is itself electrolyte tolerant and using oil soluble hydroxylic non-ionic surfactant(s) as or in the oil compatible surfactant(s) component can contribute to this (see further below).

In particular, it is desirable that:
a) the oil compatible, electrolyte tolerant surfactant component is one which will stabilise an emulsion of the electrolyte solution in the biologically efficacious oil (without requiring further surfactant) to form a water-in-oil emulsion; and
b) the water soluble surfactant component is itself soluble in the electrolyte solution and desirably will stabilise an emulsion of the biologically efficacious oil in the electrolyte solution (without requiring further surfactant), in particular so that the aqueous phase forms an oil-in-water emulsion when mixed with the oil phase including the oil compatible, electrolyte tolerant surfactant (see below for mixing methods).

Further proportions of the surfactant components are desirably within the following ranges:
c) the oil compatible surfactant [(a) above] is from 0.1 to 5, desirably 0.2 to 2, more desirably 0.3 to 1 parts by weight (pbw) surfactant per pbw of the biologically efficacious oil; and
d) the water soluble surfactant [(b) above] is from 0.1 to 10, desirably 0.5 to 5, more desirably 1 to 3, pbw per pbw of the oil compatible surfactant [(a) above].

The oil compatible surfactant component is one or more surfactant(s) which is(are) soluble or stably dispersible in the oil at a concentration that provides surfactant activity effective to stabilise an emulsion of an aqueous solution of the electrolyte in the oil. Typically, the oil compatible surfactant component is or includes a non-ionic surfactant, particularly a hydroxylic surfactant i.e. it retains one or more free hydroxyl groups, as this improves the electrolyte tolerance, and is itself either a liquid that is directly miscible in the oil or is a solid or semisolid that is soluble in the oil. Suitable oil soluble surfactants for use as or in the oil compatible surfactant component include nonionic surfactants such as polyol partial esters, particularly sorbitan (partial) esters, glycerol and polyglycerol partial esters and propylene glycol monoesters of fatty acids; alkanolamide surfactants; alkoxylated fatty alkylamines; and acid form anionic surfactants, such as alkyl sulphonates, alkylbenzene sulfonates, fatty acids, and acid form or partially neutralized (generally at an aqueous pH less than 5) alkyl phosphates and ether phosphates. Among these:

sorbitan ester surfactants are typically $C_8$ to $C_{22}$ fatty acid esters of sorbitan typical comprising mixtures of the various esters of fatty acid and sorbitan. Partial esters, especially (particularly) mono esters, which retain free hydroxyl groups thus improving aqueous electrolyte compatibility, are particularly useful, e.g. sorbitan monooleate, sesquioleate, monoisostearate, monostearate and monolaurate.

glycerol partial ester surfactants (partial glycerides) are mono- and/or di-esters of glycerol with typically $C_8$ to $C_{22}$ fatty acids. Mono-glyceride esters, which retain free hydroxyl groups thus improving compatibility with aqueous electrolytes, are particularly useful. Partial glycerides are usually available as mixtures of esters on average corresponding to the nominal ester content. Examples include glycerol monooleate, monomyristate, monoisostearate, monostearate, monolaurate, and mixed mono- and di-glycerides of fats or oils including coconut, corn, lard, rape, particularly canola, palm, palm kernel, soybean, sunflower, and tallow oils.

polyglycerol partial esters are mono-, di-, tri-, and oligoesters of polyglycerol, typically containing an average of from 2 to 10 glycerine units, with typically $C_8$ to $C_{22}$ fatty acids commonly fractionated and/or distilled fatty acids with polyglycerol. Polyglycerol partial esters retain free hydroxyl groups thus improving aqueous electrolyte compatibility. Examples include polyglycerol caprate, caprylate, laurate, myristate, palmitate, oleate, linoleate, stearate, and isostearate.

propylene glycol monoesters of fatty acids are typically with $C_8$ to $C_{22}$ fatty acids typically $C_8$ to $C_{22}$ fatty acids commonly fractionated and/or distilled fatty acids and retain a free hydroxyl group improving aqueous electrolyte compatibility. Examples include propylene glycol monocaprylate, monocaprate, monolaurate, monomyristate, monopalmitate, monooleate, and monostearate.

alkanolamide surfactants are alkanolamides, especially dialkanolamides of, particularly $C_8$ to $C_{18}$, typically fractionated and/or distilled, fatty acids. Examples include capric/caprylic, lauric, oleic, linoleic, coconut fatty acid and soya fatty acid mono- and di-ethanolamides.

acid form anionic surfactants such as:
alkylbenzene sulphonates—typically $C_8$ to $C_{18}$ monoalkyl benzenesulphonates. Examples include linear or branched dodecylbenzene, $C_{11}$ to $C_{13}$ alkylbenzene, alpha-olefin sulphonic acids and C14-C16 olefin sulphonic acids.

acid form or partially neutralized alkyl and alkylether phosphates, generally as mixed mono and diester phosphates—the acid form of phosphated $C_{12}$ to $C_{18}$ alcohol 2 to 12 mole alkoxylates, particularly ethoxylates. Examples include $C_9$ to $C_{11}$ alkyl, $C_{12}$ to $C_{15}$ alkyl, $C_{12}$ to $C_{15}$ alkyl ether, cetyl, cetyl ether, lauryl, lauryl ether, isodecyl ether, isotridecyl ether, $C_{12}$ to $C_{16}$ ether, nonylphenyl ether, and oleyl ether phosphates. At pH values typically ranging from 5 up to 14, monoester alkylether phosphates may become ionised and water soluble, and under these conditions may be used as water soluble surfactants or co-surfactants (see below).

fatty acids—typically $C_8$ to $C_{22}$ monocarboxylic acids when present at neutral to acidic pH values (when ionised at relatively alkaline pH of from 8 to 12, $C_8$ to $C_{12}$ fatty acids may also be used as water soluble surfactants or co-surfactants), though care may be needed because fatty acids may be precipitated (as water insoluble salts) by alkali earth metal ions, particularly Ca2+, as in hard water. Examples include caprylic, capric, lauric, myristic, palmitic, palmitoleic, stearic, isostearic, oleic, linoleic, linolenic, docosanoic, behenic, eicosanoic, and arachidonic acids. Separated and/or fractionated or distilled fatty acids from naturally occurring fats and oils are also useful and examples of these include fatty acids derived from coco, palm, palm kernel, rape, particularly canola, soya and corn oils, tallow and lard.

The oil compatible surfactant may be used in combination with co-surfactants such as fatty e.g. $C_8$ to $C_{22}$, alcohols.

The water soluble electrolyte tolerant surfactant is a surfactant that is soluble in the electrolyte solution at from 20 to 25° C. and desirably will stabilise an emulsion of the biologically effective oil in the electrolyte solution in combination with the aforementioned oil compatible surfactant component—sometimes even on its own, usually within a target pH or sub-range in the overall range from 2 to 12, usually from 3 to 11, and more usually from 4 to 10. Typically surfactant combinations used in the invention will show such stability within the range pH 5 to 9.

Desirably the water soluble surfactant is soluble (and surface active) in a saturated or near saturated aqueous solution of the electrolyte agrochemical across the temperature range from 5 to 30° C., more desirably from 0 to 50° C. Suitable surfactants can be nonionic or ionic, particularly anionic or amphoteric, surfactants. Although water soluble cationic surfactants might provide some of the desired technical effects; they have undesirable environmental and toxicological properties and can contribute to compatibility problems in tank mixes, particularly complex tank mixtures and are, thus, not desirable, and are desirably absent.

Among nonionic surfactants, those including free hydroxyl groups, commonly based on saccharides, such as sugar, particularly glucose, e.g. hydrocarbyl polysaccharides and water soluble polyglycerol and sorbitol derivatives e.g. sorbitol or polyglycerol fatty acid esters having at least one free OH group for each 2 carbon atoms in the functional hydrophobe chain. Among anionic surfactants, high monoester content alkyl ether phosphates of short to medium chain length are especially effective as well as tetrasodium dicarboxyethyl stearyl sulfosuccinamate and alkyldiphenyloxide disulfonates where there is a potential molar charge density of greater than 1 depending on formulated product pH. Among amphoteric surfactants, alkyl iminodipropionates and alkyl amphopropionates are desirable.

Typical water soluble surfactants are: hydrocarbyl polysaccharides (conventionally called hydrocarbyl "polysaccharides" even where the "polysaccharide" moiety contains few or even only one saccharide unit—they are more systematically called hydrocarbyl "oligosaccharides") are typically mixtures of compounds with mono-, di- and higher oligo-/poly-saccharide units; and desirably are alkyl polysaccharides, especially alkyl polyglycosides.

We particularly use compounds of the formula (and mixtures): $R^1OG_a$, where $R^1$ is hydrocarbyl; G is a saccharide residue; and a is (an average value) of at least 1. $R^1$ is desirably, optionally substituted, alkyl, cycloalkyl, aryl, alkaryl, aralkyl or alkenyl, preferably alkyl, and suitably contains from 4 to 22, more usually up to 18, particularly from 6 to 18 and especially from 8 to 12, carbon atoms. $R^1$ can be mixed alkyl groups containing, on average, from 8 to 14 carbon atoms. The saccharide residue G may be derived from one or more of fructose, glucose, mannose, galactose, telose, gulose, allose, altrose, idose, arabinose, xylose, lyxose and ribose or from mixtures of these. The group G is particularly derived from glucose units and the compounds are then glucosides. If derived from sucrose the groups will comprise fructose and glucose residues. The value of a is the degree of polymerisation and typically will be at least 1.1, desirably at least 1.2 and particularly at least 1.3, but typically not more than 8, particularly not more than 4, for example not more than 2. When the glycoside is an alkyl glucoside, the value of a is desirably between 1 and 2.

Particularly useful alkyl polyglucoside are the formula:

$$C_bH_{(2b+1)}.O.(C_6H_{10}O_5)_c.H$$

where b is from 8 to 14, particularly from 8 to 12 and especially 9 to 10, and c is (an average value) from 1 to 2, usually at least 1.3 and not more than 1.9. A particularly useful material has b is from 8 to 11 with an average value of 9 to 10 and c from 1.35 to 1.85.

Surfactant hydrocarbyl saccharides are commercially available and the materials available under the tradenames Atplus 452 and Atplus 438 (from Uniqema) or Triton BG 10 (from Dow Chemicals) or Agrimul PG 2067 and Agrimul PG 2069 (Cognis) can be used satisfactorily.

When present, the proportion of alkyl polysaccharide in the concentrate formulations of the invention are typically from 1 to 40, desirably 2 to 35, particularly 5 to 25, wt %. As is described below in more detail other surfactants may also be included in the concentrate compositions and the total amount of surfactant is typically from 5 to 40, desirably 10 to 35, particularly 10 to 25 wt % total surfactant.

Suitable oil soluble surfactants for use with hydrocarbyl, particularly alkyl, polyglycosides include sorbitan esters; propylene glycol fatty acid esters; polyglycerol fatty acid esters; fatty alkanolamides; mixed mono- and diester alkyl ether phosphates; alkyl ether sulphates; alkylbenzene sulphonates; fatty acids; and mixtures of these.

Anionic surfactants: alkyl ether phosphate surfactants typically of the formula $[R^2(OA^1)_dO]_eP(O)OM_{(3-e)}$ where $R^2$ is a $C_8$ to $C_{18}$ alkyl group; $OA^2$ is an oxyalkylene, particularly an oxyethylene, group; d is (an average value) from 2 to 15; e is (an average value) about 1; and M is H, an alkali metal, such as sodium or potassium, or a $C_1$ to $C_3$ alkyl or $C_2$ to $C_3$ hydroxyalkyl, mono-, di-, or trisubstituted amine or ammonium group. Alkyl ether phosphates with relatively low levels of alkoxylation, may need to be kept relatively alkaline in order to maintain their water solubility (see comments above on such materials as oil soluble surfactants at relatively acid pH values).

When present, the proportion of alkyl or alkyl ether phosphate in the concentrate formulations of the invention are typically from 1 to 40, desirably 2 to 35, particularly 5 to 25, wt %.

Suitable oil soluble surfactants for use with partially or fully neutralized alkyl or alkyl ether phosphates include sorbitan esters, polyglycerol esters of fatty acids, propylene glycol fatty acid esters, fatty alkanolamides, alkoxylated fatty alkylamines, alkylbenzene sulphonates, fatty acids and mixtures of these.

alkyl dicarboxyethyl sulfosuccinamate surfactants of the formula (to be provided), particularly tetrasodium dicarboxyethyl stearyl sulfosuccinamate e.g. available as Monawet SNO-35. Suitable oil soluble surfactants for use with partially or alkyl dicarboxyethyl sulfosuccinamates include sorbitan esters, polyglycerol esters of fatty acids, propylene glycol fatty acid esters, fatty acids and mixtures of these.

acyl sarcosinate surfactants of the formula (to be provided), particularly cocoyl sarcosinate e.g. available as Crodasinic from Croda. Suitable oil soluble surfactants for use with partially or alkyl dicarboxyethyl sulfosuccinamates include sorbitan esters, polyglycerol esters of fatty acids, propylene glycol fatty acid esters, fatty acids and mixtures of these.

alkyl diphenyl ether sulphonates, particularly $C_{10}$ to $C_{18}$, especially about $C_{12}$, diphenyl oxide (diphenyl ether) sulphonates, particularly bis-sulphonates i.e. with one sulphonate group on each phenyl ring, particularly dodecyl diphenyl oxide bis-sulphonate e.g. as available as Dowfax 2A1. Suitable oil soluble surfactants for use with alkyl diphenyl ether sulphonates include sorbitan esters, polyglycerol esters of fatty acids, propylene glycol fatty acid esters, mixed mono- and diester alkyl ether phosphates, alkyl ether sulphates, fatty acids and mixtures of these.

amphoteric surfactants—are (in the present context) ionic surfactants containing a linear or branched, saturated or unsaturated $C_4$ to a $C_{22}$ hydrocarbyl chain covalently bound to (i) at least one primary, secondary, or tertiary nitrogen atom having a free (unbonded) electron pair capable of being protonated to give net positive charge on that nitrogen, and (ii) at least one anionic functional group. Amphoteric surfactants are neutral at their isoelectric point and have either net positive charge at lower pH values and/or net negative charge higher pH values. Among such surfactants are adducts of $C_8$ to $C_{18}$ primary alkylamines and unsaturated acids and which are typically described as alkylamino mono- or alkylimino di-acids such as $C_8$ to $C_{10}$ alkyl-, 2-ethylhexyl-, laur-, tallow alkyl-, soya alkyl-, or coco alkyl-aminomono- or iminodi-propionates. Adducts of $C_5$ to $C_{22}$ fatty acids and aminoethyl ethanolamine (AEEA) (hydroxyethyl alkylimidazolines) and unsaturated acids, such surfactants are typically described as alkyl, particularly hydroxyalkyl amphoacids such as hydroxyethyl ($C_4$ to $C_8$)alkyl-, hydroxyethyl ($C_7$ to $C_9$) alkyl-, hydroxyethyl laur-, and hydroxyethyl coco-amphomono- and amphodipropionates.

When present, the proportion of amphoteric surfactant in the concentrate formulations of the invention are typically from 1 to 40, desirably 2 to 35, particularly 5 to 25, wt %.

Suitable oil soluble surfactants for use in conjunction with amphoteric surfactants include mixed mono- and di-ester alkyl ether phosphates, alkyl ether sulphates, sorbitan esters, fatty acid partial glycerides, fatty acid polyglycerol esters, propylene glycol fatty acid esters, fatty alkanolamides, alkoxylated fatty alkylamines, alkylbenzene sulfonates, fatty acids and mixtures of these.

In practice, alkyl ether phosphate surfactants are commonly commercially available as mixtures of mono- and di-alkyl ether phosphate esters. This opens the possibility of controlling the pH so that the mono-phosphate is ionised, but the di-phosphate remains un-ionised in the acid form. Such a combination can be effective to provide both the oil and water soluble surfactants as used in this invention.

The electrolyte compatible and water soluble surfactant may be used in combination with hydrotroping surfactants such as sodium, potassium, and ammonium mono- and di($C_1$ to $C_4$) alkylbenzenesulfonates, mono- and di-(2-butoxyethoxyethyl) phosphates, or $C_4$ to $C_{10}$ fatty alkyl carboxylates.

Additional surfactant(s), particularly non-ionic surfactants or anionic surfactants, may be included to obtain desired properties in the final composition or in the spray formulation upon dilution e.g. wetting, foam resistance etc. (of course provided that they do not make the concentrate unstable).

The total amount of surfactant in the concentrate is typically from 2.5 to 25 wt % total surfactant based on the total formulation. It may be more practically useful to consider total surfactant concentration in relation to the proportion of oil in the formulation, so that at the general lower end of overall oil concentration of about 1% the proportion of surfactant will typically be about 2.5 parts by weight (pbw) surfactant to 1 pbw oil and at the general upper end of oil concentration of 40 to 50% the proportion of surfactant will typically be about 1 pbw surfactant to 2 pbw oil.

Water is included in the concentrate composition to dissolve the electrolyte agrochemical (fertilizer and/or pesticide) and the polyol or saccharide component (when present) and may aid solublisation of the stabilising surfactant, particularly the water soluble component. The amount of water used is sufficient to dissolve these components, but is desirably sufficiently low for the composition to remain homogenous for at least 24 hours after being made.

Within these guidelines we have found it desirable to use as little water (including water that is supplied to the formulation as solvent or carrier for other components) as is practical—generally limited to the amount required to dissolve (and retain in solution) the electrolyte agrochemical across a desired range of temperatures. Overall the total amount of water present is generally not more than 60%, particularly not more than 45%, and desirably from 15 to 35% by weight of the total formulation. Amounts of less that about 15% reduce the ability to carry an efficacious amount of the water soluble electrolyte agrochemical. The (relatively) higher proportions of water will generally be suitable for incorporating solid fertilizer materials such as ammonium sulfate, urea, ammonium nitrate or ammonium phosphate.

The components and their proportions are preferably chosen such that where any components are readily available (only) as aqueous solutions, such as high fructose corn syrup (HFCS) (see the discussion of polyols below), the composition provided by mixing the composition components is stable, notwithstanding the water which is thereby introduced. The concentrate will usually be a solution of the oil in the water, the surfactant combination acting to solublise the oil, or as an oil-in-water colloidal emulsion or a microemulsion in which the oil is dispersed as very fine droplets such that the composition is clear or transparent.

The electrolyte agrochemical is typically either or both of a fertilizer, particularly a water soluble inorganic fertilizer, or a water soluble ionic pesticide (electrolyte pesticide), usually a herbicide, and most commonly a foliar applied (post-emergence) herbicide when present. Typically the concentration of electrolyte in the concentrate composition is from 1 to 50%, more usually 5 to 40%, particularly 10 to 30% by weight of the total composition.

Among water soluble fertilisers that for electrolyte solutions in water are the common water soluble inorganic fertilizers that provide nutrients such as nitrogen, phosphorus, potassium or sulphur. Examples of such fertilizers include:

for nitrogen as the nutrient:
nitrates and or ammonium salts such as ammonium nitrate, calcium ammonium nitrate (in the solid form: $[Ca(NO_3)_2]_5.NH_4(NO_3)_2.10H_2O$), ammonium sulphate nitrate, ammonium phosphates, particularly mono-ammonium phosphate ($NH_4H_2PO_4$), di-ammonium phosphate ($[NH_4]_2HPO_4$), and ammonium polyphosphate, ammonium sulphate, and the less commonly used calcium nitrate, sodium nitrate, potassium nitrate and ammonium chloride;

for potassium as the nutrient:
potassium chloride, potassium sulphate, for example as the mixed sulphate with magnesium ($K_2SO_4.MgSO_4$), potassium phosphates, particularly potassium dihydrogen phosphate ($KH_2PO_4$) and potassium polyphosphate (commonly given the formula $(KPO_2)_x$) and less commonly potassium nitrate;

for phosphorus as the nutrient:
acidic forms of phosphorus such as phosphoric, pyrophosphoric or polyphosphoric acids can be used, but are not particularly preferred because of their acidity and corrosiveness, and salt forms will usually be preferred such as ammonium phosphates, particularly mono-ammonium phosphate, di-ammonium phosphate, and ammonium polyphosphate, potassium phosphates, particularly potassium dihydrogen phosphate and potassium polyphosphate;

for sulphur as the nutrient:
ammonium sulphate and potassium sulphate, e.g. the mixed sulphate with magnesium.

Other water soluble nutrient containing compounds (commonly identified as "micronutrients") may also be included in the compositions e.g. to provide minor or trace nutrients to the formulation. Similarly, water soluble buffering and chelating agents such as ammonium and alkali metal citrates, gluconates, lactates, and polyacrylates may be included as part or all of the electrolyte component of the formulation.

When present, the fertiliser is typically included as a concentrated aqueous solution e.g. having a concentration of 10 to 90, particularly 10 to 40% by weight and the proportion of anhydrous fertiliser in the total concentrate formulation is typically from 5 to 40, more usually, 10 to 35, particularly 15 to 30, % by weight based on the concentrate.

Water soluble ionic pesticides include particularly water soluble non-selective herbicides such as the glyphosate, gluphosinate and paraquat and diquat types. The well known and widely used broad spectrum glyphosate type of herbicides are N-phosphono-methyl-N-carboxyalkyl compounds, particularly N-phosphonomethyl glycines, usually as a water soluble agrochemically acceptable salt, commonly alkali metal e.g. sodium or potassium or amine e.g. isopropylamine, or trimesium, salts. The gluphosinate type of herbicides are phosphinyl amino acids such as Glufosinate [2-amino-4-(hydroxymethylphosphinyl) butanoic acid] particularly as the ammonium salt. For both the glyphosate and gluphosinate types of herbicide, the main active component is present in aqueous solution as an anion (or overall negatively charged zwitterion). The paraquat and diquat types of herbicides are bipyridinium compounds particularly Paraquat [1,1'-dimethyl-4,4'-bipyridinium] and Diquat [1,1'-dimethyl-2,2'-bipyridinium]. This type of compound is present in aqueous solution as a cationic ammonium species.

When present, the electrolyte pesticide it typically included in the concentrate compositions typically from 1 to 50%, more usually, 5 to 40%, particularly 5 to 35% by weight based on the concentrate.

Overall, the concentration of the water soluble electrolyte agrochemical will typically be at least 5% for materials that are less soluble in water such as triammonium phosphate and up to 50% by weight for more water soluble materials e.g. urea and/or ammonium nitrate. Generally the concentration will be close to saturation as this gives the highest concentration of this material in the concentrate formulation. The saturation concentration (usually between 0 and 50° C.) in combination with the amount of water included in the formulation determine the amount of water soluble electrolyte agrochemical. Generally, it is particularly useful to make the concentrates using (premixed) aqueous solutions of the water soluble electrolyte agrochemicals as near as is practically possible to their saturation concentration at about 20° C.

The concentrate further desirably includes a polyol component to improve fluid viscosity, compatibility, ease of dispersion in spray mixtures and concentrate stability. The polyol component is a non-surfactant material having multiple free OH groups and will usually be provided to the formulation as a liquid component conveniently included by mixing it with the electrolyte solution to form a stable premixture.

The polyol can be a simple polyhydroxy material such as a glycol e.g. ethylene or propylene glycol, glycerol, polyglycerol or polyols such as sorbitol, pentaerythritol, trimethylol ethane or trimethylol propane. Where the polyol is a liquid e.g. ethylene or propylene glycol, glycerol or polyglycerol, it may be used as neat material, and where the polyol is solid it will usually be used as a solution in water or a suitable organic solvent such as a glycol e.g. ethylene or propylene glycol or glycerine. When the polyols are used as aqueous or organic solutions, the solutions typically have a polyol concentration of from 50 to 95% by weight.

When used the polyol is typically present in an amount of from 1 to 25, more usually from 2 to 15, and particularly from 3 to 10, % by weight of the concentrate formulation.

As well as simple polyols, saccharides may be used, and because saccharides are generally solids, they will usually be used as solutions. The saccharide may be a monosaccharide, oligosaccharide or a polysaccharide or mixture of these and the saccharides may be linear, branched, or cyclic. Functional saccharides are also useful and include either or both acid and amine functional sugars such as N-methylglucamine, gluconic acid, and glutaric acid. Where the saccharide is a solution, the solvent may be water or an organic hydrophilic solvent such as propylene glycol, or glycerol or mixtures of these, but is desirably water. Such liquid saccharide solutions are commonly called "syrups". Oligosaccharides present in solution are commonly called maltodextrins while polysaccharides are commonly called dextrins. Among liquid saccharide solutions, materials of particular use in this invention include compounds and mixtures of compounds described as corn syrup, HFCS (high fructose corn syrup), corn sweetener, invert sugar, invert sugar syrup, sugar, sugar syrup, glucose, fructose, sucrose, lactose, maltose, corn syrup solids and maltodextrins. Such liquid saccharide solutions are generally homogeneous and stable for at least 24 hours. Typically saccharide solutions used in this invention contain from 20 to 40% by weight of water.

Desirable oligosaccharides are of the general formula: $HO.(C_6H_{10}O_5)_n.H$ where n is (an average value) of from 1 to 50. In particular, the saccharide may be one in which the average value of n is from 1 to 5. A particularly useful material of this type has n of approximately 1 and where the saccharide is a monosaccharide keto-sugar, particularly fructose. Fructose is commercially available as HFCS and the material designated for example as IsoClear 55 by Cargill can be used satisfactorily.

The saccharide is typically included in the concentrate compositions from 1 to 30, more usually, 5 to 20, particularly 5 to 15% by weight based on the concentrate. Expressed as the liquid saccharide the amount used is typically up to about 20% by weight of the concentrate formulation.

A further optional component that may be included to improve compatibility, stability and/or bioperformance of the concentrate formulations is one or more polyelectrolyte polymers. Suitable polymers are those which are soluble in the, typically saturated or near saturated, electrolyte solutions, and can include water soluble polyacrylates maleate polymers and copolymers e.g. styrene maleic anhydride copolymers, maleic-acrylic copolymers and sulphonated polystyrenes. When used the polyelectrolyte polymer is typically present in an amount of from 1 to 20, more usually from 1 to 10, and particularly from 1 to 5, % by weight of the concentrate formulation.

The concentrate formulation may also include one or more of other surfactants, particularly non-ionic and/or anionic surfactants, and/or additives such as antifoam or foam suppressant materials. As is noted above, the inclusion of silicone antifoam materials may cause minor haziness or milkiness in the concentrate formulation because the silicone is not completely homogeneously dissolved in the formulation. On dilution the silicone will come out of solution and migrate to the liquid/air interface so as to effect the desired foam control.

The relative proportions of the components of the formulation are desirably as follows:

| | Component | Ranges (parts by weight) | | |
|---|---|---|---|---|
| | | Broad | Desired | Preferred |
| a | biologically efficacious oil | 0.5 to 50 | 5 to 40 | 10 to 35 |
| b | agrochemical electrolyte | 1 to 50 | 5 to 40 | 5 to 35 |
| c | stabilising surfactant | 1 to 40 | 2 to 35 | 5 to 25 |
| d | polyol (when present) | 1 to 25 | 2 to 15 | 3 to 10 |
| e | saccharide (when present) | 1 to 30 | 5 to 20 | 5 to 15 |
| f | polyelectrolyte polymer (when present) | 1 to 20 | 1 to 10 | 1 to 5 |
| g | total water | 15 to 60 | 15 to 45 | 15 to 35 |

The concentrate is typically a light yellowish to amber readily pourable (at ambient temperature) liquid of relatively low fluid viscosity suitable for pumping and bulk handling. Particularly desirable compositions are stable across a temperature range from about −10° C. to about 50° C. for a period of 30 days and show acceptable dilution stability i.e. no oil separation and minimal creaming or sedimentation when diluted between 1 and 2.5% by volume even in 50, 342, and 1000 ppm hardness waters.

The concentrate formulations of the invention can in many instances be successfully made up by directly mixing the components together in an unspecified order. Usually simple mixing will be adequate to form the homogeneous concentrate although the use of specified premixes and particular orders of addition typically show better results.

Greatest product consistency is provided when a form of emulsion inversion processing is applied. The inversion process may desirably be done either by: (1) changing the differential solubility of the selected surfactant composition by increasing or decreasing the degree of ionization for initially unneutralized or uncharged ionic surfactants, or (2) by progressively changing the ratio of water soluble electrolyte tolerant surfactant to oil compatible electrolyte tolerant surfactant.

For ionic surfactants, phase inversion may be carried out by solubilizing for example mixed mono-diester alkyl ether phosphate in the biologically efficacious oil at a desired concentration, often between 25% and 75% of the total finished oil and surfactant premixture weight. This premixture subsequently may be dispersed with shear into the target concentrated electrolyte, already containing any optional polyols, saccharides, or polymers. Alternatively, for acid mono- and diester alkyl ether phosphate surfactants an alkalizing agent e.g. ammonium or potassium hydroxide, mono- di- or triethanolamine may be gradually added to reach a total amount sufficient to achieve a target pH (greater than 5, often between 5.5 and 8.5) during which the dispersion increases in homogeneity and rises in viscosity until it passes through its inversion point to becomes a stable microemulsion.

In the case of completely nonionic systems or fully charged ionic species e.g. neutralized anionic, and neutralized amphoteric surfactants (typically already in aqueous solution at between 25 and 70% active surfactant by weight) the surfactant solution can be gradually added to reach a total amount sufficient to drive the mixture through its inversion point to become a stable microemulsion.

The concentrate formulations of the invention will generally be used by first being diluted with water to generate an agricultural spray mixtures containing an agrochemical which is then used to treat crops (or land where crops are to be grown) including to fertilize crops and to kill weeds in or pests on crops, by spraying. Such spray mixtures will contain one or more pesticidally active ingredients and/or nutrients.

The invention further includes a diluted formulation which comprises a composition comprising components (a), (b) and (c) according to the invention with from about 10 to about 10,000 times the weight of the composition of water. The concentrate compositions of the invention emulsify readily on dilution in water to form the formulation. At relatively low levels of dilution, the diluted product will be an oil-in-water emulsion having a relatively high concentration of oil. This intermediate emulsion subsequently can be further diluted by water or an aqueous solution or suspension of other components desired in the final formulation.

In a further aspect, the invention provides a method of applying a formulation of the invention to a substrate. Embodiments of this method include a method of treating vegetation, particularly a crop or weeds in soil in which a crop is sown subsequently, by applying to plants and/or soil a diluted concentrate formulation of the invention which comprises an agrochemical.

The agrochemical may be one or more growth regulators, herbicides, and/or pesticides, for example insecticides, fungicides or acaricides and the invention accordingly includes:

a) a method of killing or inhibiting vegetation by applying a diluted concentrate of the invention which comprises one or more growth regulator and/or herbicide, and
b) a method of killing or inhibiting plant pests by applying the a diluted concentrate of the invention which comprises one or more pesticides, for example insecticides, fungicides or acaricides.

In this embodiment, the effect of the agrochemical, whether one or more growth regulators, herbicides, and/or pesticides, for example insecticides, fungicides or acaricides, may be potentiated by the oil component and/or the saccharide and/or the surfactant composition present in the composition.

The agrochemical may be one or more fertiliser and/or plant nutrient and/or micronutrient and the invention accordingly includes:
c) a method of treating vegetation or the soil in which a crop is subsequently sown by applying a diluted concentrate of the invention which comprises at least one fertiliser and/or plant nutrient and/or micronutrient.

Desirably the agrochemical is a combination of one or more growth regulators and/or herbicides and/or pesticides with a fertiliser and/or plant nutrient and/or micronutrient and the invention accordingly includes:
d) a method of treating vegetation or the soil in which a crop is subsequently sown by applying a diluted concentrate of the invention which comprises at least one growth regulators and/or herbicides and/or pesticide and at least one fertiliser and/or plant nutrient and/or micronutrient.

The following Examples illustrate the invention. All parts and percentages are by weight unless otherwise indicated.

Materials
Surfactants
　Oil Soluble Surfactants
OSS1 nonylphenol 9-ethoxylate, Renex 698, ex Uniqema
OSS2 sorbitan monolaurate, Span 20, ex Uniqema
OSS3 C12/15 alcohol 4-ethoxylate, nonionic surfactant, Synperonic A4, ex Uniqema
　Fatty Acid Co-surfactants
FA1 oleic acid
FA2 tall oil fatty acids, Pamak MFAF, ex Hercules
　Water Soluble Surfactants
WSS1 $C_{9/11}$ alkylpolyglycoside, nonionic surfactant (50% active), Atplus 438, ex Uniqema
WSS2 $C_{8/10}$ alkylpolyglycoside, nonionic surfactant (70% active), Atplus 452, ex Uniqema
WSS3 sodium lauriminodipropionate, amphoteric surfactant, Monateric 1188M, ex Uniqema
WSS4 C8/10 alkyl polyoxyethylene ether (mono)phosphate, anionic surfactant, Monafax 1214, ex Uniqema
　Oils
Oil1 paraffinic mineral oil, Sun 7N, ex Sunoco
Oil2 methyl oleate ester oil, Priolube 1400/1530, ex Uniqema
Oil3 d-limonene terpene oil, ex Florida Chemicals
Oil4 isoparaffinic mineral oil, Isopar M, ex ExxonMobil
Oil5 aromatic naphtha oil, Aromatic 150, ex ExxonMobil
Oil6 a blend of 50 wt % Oil1, 25 wt % Oil5 and 25 wt % Oil3
Oil7 methylated soybean oil, ex Soy Power
　Electrolytes
Elec1 ammonium sulphate (anhydrous)
　Polyols
Pol1 high fructose corn syrup 77% solids 55% fructose (dry basis), IsoClear 55, ex Cargill
Pol2 hexylene glycol Test Methods
Stability Testing
Samples of formulated adjuvants were subjected to storage testing to assess their stability over extended periods or non-ambient temperatures. The storage conditions are indicated in abbreviated form as Time/Temp—times in days (D) or weeks (W) and temperatures are indicated as amb=ambient or in ° C. Samples are assessed as stable if they remain clear over the storage period, no sep=no visible separation of the stored sample confirming excellent stability. Samples which are not fully stable on extended storage are noted as hazy/cloudy (sl=slightly; v sl=very slightly) or by the amount of separation by volume (as a % figure) bs=bottom separation and ts=top separation.

Methods of Making Up Formulations
　No Neutralisation Required
　　For systems where there no pH neutralization is required—primarily nonionic systems—the oil soluble nonionic surfactant is dissolved in the target oil at the desired rate and this solution is subsequently added to the aqueous electrolyte solution under moderate to high agitation in order to form a dispersion. Where a polyol or polyelectrolyte polymer is included, it will usually be dissolved in the electrolyte solution. The appropriate amount of water soluble electrolyte tolerant surfactant is added to the dispersion under moderate to high agitation to maintain shear while minimizing air entrainment and foaming. In a variation of this method, the water soluble electrolyte tolerant surfactant is added to the aqueous electrolyte solution prior to the addition of surfactant/oil mixture and agitation is maintained until the (oil soluble) surfactant/oil mixture is fully added and the system becomes transparent (or only slightly hazy or cloudy depending on the presence of deliberately added dispersed phases e.g. silicone oils as foam control agents). An advantage of the former approach over the latter is that there is less tendency for excess foam generation when the electrolyte soluble surfactant is added last.

Neutralisation Required
　　For systems where there is pH adjustment is required e.g. in systems including anionic surfactant, the oil soluble/dispersible surfactant(s) is(are) combined with the target oil at the desired rate and dispersed/dissolved under moderate shear. The surfactant/oil mixture is added to the aqueous electrolyte solution under moderate to high shear agitation in order to form a dispersion. Where polyol or polyelectrolyte polymers are included these will usually be dissolved in the aqueous electrolyte solution. The pH adjusting agent e.g. alkali such as aqueous ammonium or potassium hydroxide or alkyl/alkanolamine, is subsequently added to the dispersion under moderate to high agitation until the target pH is reached, during which time agitation is adjusted to maintain shear while minimizing air entrainment and foaming. Target pH varies (typically between 5 and 9) based on the chemical stability of other formulation additives at high or low pH as well as the target viscosity and cloud point of the resulting homogenous system. In this method the water soluble surfactant is typically added to the electrolyte solution. In this method the water soluble surfactant is typically added to the electrolyte solution at the start of mixing and after the oil soluble surfactant is dissolved/dispersed in the oil. In a variation of this method the pH adjustment agent is added to the aqueous electrolyte solution prior to the addition of surfactant:oil mixture and agitation is continuously applied until the full charge of surfactant:

oil is added and the system achieves substantial transparency. Typically either the neutralizing agent or the unneutralized surfactant are added gradually during mixing and until the complete charge of either component has been added. Generally, mixing will be maintained throughout the addition to avoid the formation of high viscosity and poorly dispersible surfactant gels in regions where surfactant neutralization has taken place.

In either case, the final stable formulations are substantially transparent liquid that either remains transparent or whitens ("blooms") upon dilution in water (of various hardness).

EXAMPLE 1

Crop oil/surfactant concentrate (COC) formulations were made up as described above (no neutralisation) dissolving the oil compatible surfactant and co-surfactant in the crop oil at 40% by weight. In each case the COC was a clear yellowish liquid which was stable and self-emulsifying on dilution with water. Separately, ammonium sulphate was dissolved in water to give a 40 wt % aqueous solution and this electrolyte solution mixed with the COC and the alkylpolysaccharide water soluble surfactant and high fructose corn syrup was added under agitation to give the final combined adjuvant formulation. The materials used and amounts (weight percentages on the overall formulation) are set out in Table 1 below.

TABLE 1

| Ex No | oil soluble surfactant type | wt % | co-surfactant type | wt % | Oil type | wt % | water soluble surfactant type | wt % | electrolyte type | wt % | polyol type | wt % | water* (wt %) |
|---|---|---|---|---|---|---|---|---|---|---|---|---|---|
| Ex 1.1 | OSS1 | 2.2 | FA1 | 2.2 | Oil1 | 6.7 | WSS1 | 9.1 | Elec1 | 28.2 | Pol1 | 9.2 | 42.3 |
| Ex 1.2 | OSS1 | 2.1 | FA2 | 2.4 | Oil7 | 6.8 | WSS1 | 9.0 | Elec1 | 28.2 | Pol1 | 9.2 | 42.3 |

*the amount of water in this column is that used to dissolve the electrolyte and does not include any water present in other components (in particular the high fructose corn syrup and the alkyl polysaccharide surfactant).

The electrolyte containing COC adjuvant formulation of Example 1.1 was a slightly hazy dark brown solution and Example 1.2 a dark brown solution with a greenish tint. Both formulations were stable at ambient temperature and readily emulsified on dilution with water.

EXAMPLE 2

An aqueous electrolyte fertilizer solution was made up from the following components:

|  | parts by weight | wt % |
|---|---|---|
| ammonium sulphate | 960 | 33.7 |
| water | 1440 | 50.5 |
| HFCS | 450 | 15.8 |

Crop Oil Concentrates were made up using Oil1 oil compatible surfactant (OSS1) and co-surfactant (FA1) as follows:

|  | wt % |
|---|---|
| Oil1 | 60 |
| OSS1 | 20 |
| FA1 | 20 |

The final adjuvant formulations were made up as generally described above (for nonionic surfactants), using an alkyl polysaccharide surfactant (WSS1) as the water soluble surfactant using the weight proportions of formulation components set out in Table 2a below.

TABLE 2a

| Ex No | Electrolyte solution | COC | WSS | Total |
|---|---|---|---|---|
| 2.1 | 450 | 100 | 75 | 625 |
| 2.2 | 400 | 150 | 100 | 650 |
| 2.3 | 350 | 200 | 125 | 675 |
| 2.4 | 105 | 105 | 50 | 260 |
| 2.5 | 400 | 150 | 113 | 663 |

The overall percentage composition of the final adjuvant compositions and their properties are set out in Tables 2b and 2c below.

TABLE 2b

| Ex No | Elec1 | Oil1 | Water | Pol1 | WSS1 | OSS1 | FA1 |
|---|---|---|---|---|---|---|---|
| 2.1 | 24.25 | 9.6 | 36.38 | 11.37 | 12 | 3.2 | 3.2 |
| 2.2 | 20.73 | 13.85 | 31.1 | 9.72 | 15.38 | 4.62 | 4.62 |
| 2.3 | 17.46 | 17.78 | 26.2 | 8.19 | 18.52 | 5.93 | 5.93 |

TABLE 2b-continued

| Ex No | Elec1 | Oil1 | Water | Pol1 | WSS1 | OSS1 | FA1 |
|---|---|---|---|---|---|---|---|
| 2.4 | 13.6 | 24.23 | 20.41 | 6.38 | 19.23 | 8.08 | 8.08 |
| 2.5 | 20.32 | 13.57 | 30.49 | 9.53 | 17.04 | 4.52 | 4.52 |

TABLE 2c

| Ex No | Appearance Initial | 4 W/Amb | 4 W/50° C. |
|---|---|---|---|
| 2.1 | v sl cloudy | v sl hazy, no separation | 30% bs |
| 2.2 | v sl cloudy | v sl hazy, 5% bs | 25% bs |
| 2.3 | clear dark brown | Clear dark brown, no sep | 20% bs |
| 2.4 | clear dark brown | Clear dark brown, 5% bs | 20% bs |
| 2.5 | clear dark brown | Clear dark brown, no sep | Clear no sep |

EXAMPLE 3

Further formulations were made up to test variation in the proportions of oil compatible surfactant and co-surfactant using the aqueous electrolyte fertilizer solution used in Example 2. The Crop Oil Concentrates were made up using 60 wt % Oil1 and 40 wt % combined oil compatible surfactant (OSS1) and co-surfactant (FA1) as set out in Table 3a below:

TABLE 3a

| Ex No | Oil1 wt % | OSS1 wt % | FA1 wt % |
|---|---|---|---|
| 3.1 | 60 | 10 | 30 |
| 3.2 | 60 | 15 | 25 |
| 3.3 | 60 | 19 | 21 |
| 3.4 | 60 | 17 | 23 |

The final adjuvant formulations were made up as generally described above (for nonionic surfactants), using an alkyl polysaccharide surfactant (WSS1) as the water soluble surfactant using the proportions of formulation components (parts by weight) set out in Table 3b below:

TABLE 3b

| Ex No | Electrolyte soln (pbw) | COC (pbw) | WSS2 (pbw) |
|---|---|---|---|
| 3.1 | 95 | 15 | 14 |
| 3.2 | 95 | 15 | 14 |
| 3.3 | 95 | 15 | 14 |
| 3.4 | 95 | 15 | 14 |

The overall percentage composition of the final adjuvant compositions and their behaviour under test storage conditions are set out in Tables 3c and 3d below:

TABLE 3c

| Ex No | Elec1 | Oil1 | Water* | Pol1 | WSS1 | OSS1 | FA1 |
|---|---|---|---|---|---|---|---|
| 3.1 | 25.8 | 7.26 | 38.71 | 12.1 | 11.29 | 1.21 | 3.63 |
| 3.2 | 25.8 | 7.26 | 38.71 | 12.1 | 11.29 | 1.81 | 3.02 |
| 3.3 | 25.8 | 7.26 | 38.71 | 12.1 | 11.29 | 2.3 | 2.54 |
| 3.4 | 25.8 | 7.26 | 38.71 | 12.1 | 11.29 | 2.06 | 2.78 |

*water = added water

TABLE 3d

| Ex No | Appearance | | |
|---|---|---|---|
| | Initial | 1 W/amb | 4 D/50° C. |
| 3.1 | Clear | Clear | Clear |
| 3.2 | Clear | Clear | Clear |
| 3.3 | Clear | Clear | Clear |
| 3.4 | Clear | Clear | Clear |

EXAMPLE 4

An aqueous electrolyte fertilizer solution was made up from the following components:

| | parts by weight | wt % |
|---|---|---|
| Pol1 | 300 | 15.8 |
| Elec1 | 640 | 33.7 |
| water | 960 | 50.5 |

Portions of this solution were formulated as described above into three electrolyte/crop oil adjuvant combinations labelled "A", "B" and "C" having the compositions (wt %) set out in Table 4a below:

TABLE 4a

| Ex No | Oil1 (wt %) | OSS2 (wt %) | WSS1 (wt %) | Pol1 (wt %) | Elec1 (wt %) | water (wt %) |
|---|---|---|---|---|---|---|
| 4A | 21 | 3 | 6 | 11.05 | 23.58 | 35.37 |
| 4B | 12 | 12 | 6 | 11.05 | 23.58 | 35.37 |
| 4C | 12 | 3 | 15 | 11.05 | 23.58 | 35.37 |

Portions of these three combinations were mixed in the proportions set out in Table 4b below to give stable formulations. Table 4b also includes the calculated percentage composition of the adjuvant formulations:

TABLE 4b

| Ex No | A (pbw) | B (pbw) | C (pbw) | Pol1 (%) | Elec1 (%) | Water (%) | Oil1 (%) | OSS2 (%) | WSS1 (%) |
|---|---|---|---|---|---|---|---|---|---|
| 4.1 | 12 | 2.5 | 5.5 | 11.05 | 23.58 | 35.37 | 17.4 | 4.13 | 8.48 |
| 4.2 | 10 | 3 | 7 | 11.05 | 23.58 | 35.37 | 16.5 | 4.35 | 9.15 |
| 4.3 | 8 | 3 | 8.5 | 11.05 | 23.58 | 35.37 | 15.6 | 4.58 | 9.83 |
| 4.4 | 6 | 4 | 10 | 11.05 | 23.58 | 35.37 | 14.7 | 4.8 | 10.5 |
| 4.5 | 4 | 4 | 12 | 11.05 | 23.58 | 35.37 | 13.8 | 4.8 | 11.4 |
| 4.6 | 2 | 6 | 12 | 11.05 | 23.58 | 35.37 | 12.9 | 5.7 | 11.4 |
| 4.7 | 2 | 4 | 14 | 11.05 | 23.58 | 35.37 | 12.9 | 4.8 | 12.3 |
| 4.8 | 0 | 6 | 14 | 11.05 | 23.58 | 35.37 | 12 | 5.7 | 12.3 |
| 4.9 | 0 | 4 | 16 | 11.05 | 23.58 | 35.37 | 12 | 4.8 | 13.2 |

All these formulations were stable for 24 hours at Ambient temperature.

EXAMPLE 5

Alkaline solvent microemulsion concentrates were made up as follows. Seven electrolyte/crop oil adjuvant combinations labelled "A1", "A2", "A3", "B1", "B2", "C1", "C2" and "C3", having the following percentage compositions:

| Material | Oil6 | WSS4 | WSS3 | OSS3 | Pol2 | KOH | water | Total |
|---|---|---|---|---|---|---|---|---|
| A1 | 50 | 28 | 0 | 0 | 7 | 29.3 | 35.8 | 150 |
| A2 | 50 | 14 | 14 | 0 | 7 | 29.3 | 35.8 | 150 |
| A3 | 50 | 14 | 0 | 14 | 7 | 29.3 | 35.8 | 150 |
| B1 | 50 | 31.5 | 0 | 0 | 3.5 | 29.3 | 35.8 | 150 |
| B2 | 50 | 15.75 | 0 | 15.75 | 3.5 | 29.3 | 35.8 | 150 |
| C1 | 50 | 35 | 0 | 0 | 0 | 29.3 | 35.8 | 150 |
| C2 | 50 | 17.5 | 17.5 | 0 | 0 | 29.3 | 35.8 | 150 |
| C3 | 50 | 17.5 | 0 | 17.5 | 0 | 29.3 | 35.8 | 150 | were made up generally as described above. Portions of these seven combinations were mixed in the proportions set out in Table 5a below to give stable formulations.

TABLE 5a

| Ex No | A1 (pbw) | A2 (pbw) | A3 (pbw) | B1 (pbw) | B2 (pbw) | C1 (pbw) | C2 (pbw) | C3 (pbw) |
|---|---|---|---|---|---|---|---|---|
| 5.1 | 60 | 20 | 20 | — | — | — | — | — |
| 5.2 | 50 | 50 | 0 | — | — | — | — | — |
| 5.3 | — | — | — | 100 | 0 | — | — | — |
| 5.4 | — | — | — | 50 | 50 | — | — | — |
| 5.5 | — | — | — | — | — | 33.3 | 33.3 | 33.3 |
| 5.6 | — | — | — | — | — | 0 | 50 | 50 |

The calculated percentage composition of the stable adjuvant formulations is set out in Table 5b below.

TABLE 5b

| Ex No | Oil6 (% wt) | WSS3 (% wt) | WSS4 (% wt) | OSS3 (% wt) | Pol2 (% wt) | KOH (% wt) | Water (% wt) |
|---|---|---|---|---|---|---|---|
| 5.1 | 30 | 14.9 | 1.9 | 1.9 | 4.7 | 19.5 | 23.8 |
| 5.2 | 30 | 9.3 | 4.7 | 4.7 | 4.7 | 19.5 | 23.8 |
| 5.3 | 30 | 9.3 | 0 | 9.3 | 4.7 | 19.5 | 23.8 |
| 5.4 | 30 | 15.7 | 0 | 5.3 | 2.3 | 19.5 | 23.8 |
| 5.5 | 30 | 15.1 | 3.9 | 3.5 | 0.8 | 19.5 | 23.8 |
| 5.6 | 30 | 11.7 | 5.9 | 5.9 | 0 | 19.5 | 23.8 |

All these formulations were stable for 24 hours at Ambient temperature.

What is claimed is:

1. A stable, homogeneous liquid agrochemical concentrate, comprising:
   a) 1 to 50 wt. % of at least one biologically efficacious oil, comprising mineral oil, optionally hydrogenated vegetable oil, or ester oil;
   b) 20 to 60 wt. % water;
   c) 5 to 50 wt. % of at least one electrolyte agrochemical dissolved in the water to form concentrated aqueous electrolyte;
   d) 1 to 25 wt. % of a stabilizing surfactant composition based on a non-ionic surfactant, a non-ionic surfactant and an anionic surfactant, or an amphoteric surfactant, comprising:
      i) at least one oil compatible, electrolyte tolerant surfactant, comprising a sorbitan ester, a glycerol partial ester, a polyglycerol partial ester, a propylene glycol fatty acid monoester, an alkoxylated alkylamine surfactant, an alkanolamide surfactant, an alkylbenzene sulphonate, alkylether sulphate, an acylsarcosine, or a fatty acid; and
      ii) at least one water soluble, electrolyte tolerant surfactant, comprising a saccharide fatty acid ester, a hydrocarbyl polysaccharide, a fatty amine alkoxylate, an alkyl ether phosphate, a neutralized alkyl ether phosphate, an acylsarcosinate, an alkyl diphenyl ether sulphonate, a dicarboxy alkylsulfosuccinamate, or an alkyliminopropionate or amphopropionate amphoteric; and
   e) 1 to 40 wt. % of at least one polyol component, comprising glycols, monosaccharides, oligosaccharides, or polysaccharides;

wherein the stable, homogeneous liquid agrochemical concentrate is:
   1) capable of forming a stable dilution with water; and
   2) free from deliberately added disperse phase components.

2. The agrochemical concentrate of claim 1, wherein the at least one electrolyte agrochemical is or comprises:
   i) at least one plant nutrient material;
   ii) at least one pesticide or herbicide; or
   iii) at least one plant nutrient material and at least one pesticide or herbicide.

3. The agrochemical concentrate of claim 1, wherein the at least one oil compatible, electrolyte tolerant surfactant is a non-ionic surfactant or an acid form or partially neutralized anionic surfactant.

4. The agrochemical concentrate of claim 1, wherein the at least one water soluble, electrolyte tolerant surfactant is a non-ionic surfactant, an anionic surfactant, or an amphoteric surfactant.

5. The agrochemical concentrate of claim 1, wherein the agrochemical concentrate remains homogenous for at least 24 hours.

6. An agrochemical spray formulation, comprising the agrochemical concentrate of claim 1 diluted with from 1 to 10000 parts water per part agrochemical concentrate.

7. A method of making an agrochemical spray formulation, comprising diluting the agrochemical concentrate of claim 1 with from 10 to 1000 parts water per part agrochemical concentrate.

8. A method of treating, comprising spraying crops, soil adjacent to crop plants, or soil in which crops are to be grown with a spray formulation comprising the agrochemical concentrate of claim 1 that is diluted with from 1 to 10000 parts water per part agrochemical concentrate.

* * * * *